United States Patent
Tanaka et al.

(10) Patent No.: US 8,986,263 B2
(45) Date of Patent: Mar. 24, 2015

(54) CATHETER WITH VALVE

(75) Inventors: Takashi Tanaka, Shizuoka Prefecture (JP); Motonori Watanabe, Shizuoka Prefecture (JP); Masashige Hori, Shizuoka Prefecture (JP)

(73) Assignee: Covidien LP, Mansfield, MA (US)

( * ) Notice: Subject to any disclaimer, the term of this patent is extended or adjusted under 35 U.S.C. 154(b) by 265 days.

(21) Appl. No.: 13/412,845

(22) Filed: Mar. 6, 2012

(65) Prior Publication Data

US 2012/0232494 A1  Sep. 13, 2012

(30) Foreign Application Priority Data

Mar. 8, 2011 (JP) ................................ 2011-050890

(51) Int. Cl.
*A61M 25/00* (2006.01)

(52) U.S. Cl.
CPC ................................ *A61M 25/0075* (2013.01)
USPC ........................... 604/247; 604/246; 604/537

(58) Field of Classification Search
CPC ............ A61M 25/00; A61M 25/0054; A61M 25/007; A61M 25/0074; A61M 25/0075
USPC .................... 604/246, 247, 523, 537
See application file for complete search history.

(56) References Cited

U.S. PATENT DOCUMENTS

| | | |
|---|---|---|
| 4,403,983 A | 9/1983 | Edelman et al. |
| 4,475,898 A | 10/1984 | Brodner et al. |
| 4,493,696 A | 1/1985 | Uldall |
| 4,549,879 A | 10/1985 | Groshong et al. |
| 4,568,329 A | 2/1986 | Mahurkar |
| 4,583,968 A | 4/1986 | Mahurkar |
| 4,619,643 A | 10/1986 | Bai |
| 4,626,240 A | 12/1986 | Edelman et al. |
| 4,643,711 A | 2/1987 | Bates |
| 4,671,796 A | 6/1987 | Groshong et al. |
| 4,692,141 A | 9/1987 | Mahurkar |
| 4,701,166 A | 10/1987 | Groshong et al. |
| 4,753,640 A | 6/1988 | Nichols et al. |
| 4,769,005 A | 9/1988 | Ginsburg et al. |

(Continued)

FOREIGN PATENT DOCUMENTS

| | | |
|---|---|---|
| EP | 0 299 622 A2 | 1/1989 |
| EP | 0 299 622 A3 | 1/1989 |

(Continued)

OTHER PUBLICATIONS

English translation of Abstract for JP2001-321447.*

(Continued)

*Primary Examiner* — Laura Bouchelle
(74) *Attorney, Agent, or Firm* — John Paul Mello, Esq.

(57) ABSTRACT

A catheter with a valve is disclosed that allows smooth flow of a solution in-both when a solution is flowing from the inside of a catheter towards the outside of a catheter and when a solution is flowing from the outside of a catheter towards the inside of a catheter. The catheter includes a tubular body 12 made of an elastic and flexible synthetic resin material and is equipped with a valve having a slit 16 passing through the outer surface 12*b* of the tubular body. The catheter is also provided with the movable wall 15 sunken towards the inside of the tubular body 12 at an end tip member region 14 of the tubular body 12. The location where the movable wall 15 exists has a structure with differences in hardness in the thickness direction of the tubular body 12.

5 Claims, 4 Drawing Sheets

(56) References Cited

U.S. PATENT DOCUMENTS

| | | |
|---|---|---|
| 4,772,268 A | 9/1988 | Bates |
| 4,772,269 A | 9/1988 | Twardowski |
| 4,795,439 A | 1/1989 | Guest |
| 4,801,297 A | 1/1989 | Mueller |
| 4,808,155 A | 2/1989 | Mahurkar |
| 4,808,156 A | 2/1989 | Dean |
| 4,813,934 A | 3/1989 | Engelson et al. |
| 4,842,582 A | 6/1989 | Mahurkar |
| 4,895,561 A | 1/1990 | Mahurkar |
| 4,897,079 A | 1/1990 | Zaleski et al. |
| 4,961,809 A | 10/1990 | Martin |
| 4,973,319 A | 11/1990 | Melsky |
| 4,995,863 A | 2/1991 | Nichols et al. |
| 4,995,865 A | 2/1991 | Gahara et al. |
| 5,009,636 A | 4/1991 | Wortley et al. |
| 5,035,399 A | 7/1991 | Rantanen-Lee |
| 5,041,083 A | 8/1991 | Tsuchida et al. |
| 5,053,004 A | 10/1991 | Market et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,112,301 A | 5/1992 | Fenton, Jr. et al. |
| 5,135,599 A | 8/1992 | Martin et al. |
| 5,147,332 A | 9/1992 | Moorehead |
| 5,156,592 A | 10/1992 | Martin et al. |
| 5,160,325 A * | 11/1992 | Nichols et al. ............... 604/247 |
| 5,167,623 A | 12/1992 | Cianci et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,224,938 A | 7/1993 | Fenton, Jr. |
| 5,250,034 A | 10/1993 | Appling et al. |
| 5,261,885 A | 11/1993 | Lui |
| 5,267,979 A | 12/1993 | Appling et al. |
| 5,269,768 A | 12/1993 | Cheung |
| 5,304,155 A | 4/1994 | Lui |
| 5,308,338 A | 5/1994 | Helfrich |
| 5,346,471 A | 9/1994 | Raulerson |
| 5,348,536 A * | 9/1994 | Young et al. ............... 604/43 |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,399,172 A | 3/1995 | Martin et al. |
| 5,403,291 A | 4/1995 | Abrahamson |
| 5,405,341 A | 4/1995 | Martin |
| 5,451,206 A | 9/1995 | Young |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,522,807 A | 6/1996 | Luther |
| 5,531,679 A | 7/1996 | Schulman et al. |
| 5,554,136 A | 9/1996 | Luther |
| 5,556,390 A | 9/1996 | Hicks |
| 5,569,182 A | 10/1996 | Twardowski et al. |
| 5,571,093 A | 11/1996 | Cruz et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,718,678 A | 2/1998 | Fleming, III |
| 5,776,096 A | 7/1998 | Fields |
| 5,797,869 A | 8/1998 | Martin et al. |
| 5,807,311 A | 9/1998 | Palestrant |
| 5,807,329 A | 9/1998 | Gelman |
| 5,807,349 A | 9/1998 | Person et al. |
| 5,810,789 A | 9/1998 | Powers et al. |
| 5,830,184 A | 11/1998 | Basta |
| 5,830,196 A | 11/1998 | Hicks |
| 5,868,717 A | 2/1999 | Prosl |
| 5,928,203 A | 7/1999 | Davey et al. |
| 5,947,953 A | 9/1999 | Ash et al. |
| 5,961,485 A | 10/1999 | Martin |
| 5,961,486 A | 10/1999 | Twardowski et al. |
| 5,968,009 A | 10/1999 | Siman |
| 5,976,103 A | 11/1999 | Martin |
| 5,984,903 A | 11/1999 | Nadal |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,099,519 A | 8/2000 | Olsen et al. |
| 6,123,725 A | 9/2000 | Aboul-Hosn |
| 6,126,631 A | 10/2000 | Loggie |
| 6,146,354 A | 11/2000 | Beil |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,413,564 B2 | 8/2008 | Morris et al. |
| 2002/0090339 A1 | 7/2002 | Whalen et al. |

(56) References Cited

U.S. PATENT DOCUMENTS

| | | |
|---|---|---|
| 2002/0121282 A1 | 9/2002 | McGuskin, Jr. et al. |
| 2002/0156430 A1 | 10/2002 | Haarala |
| 2002/0165492 A1 | 11/2002 | Davey et al. |
| 2003/0032918 A1 | 2/2003 | Quinn |
| 2003/0093029 A1 | 5/2003 | McGuckin, Jr. et al. |
| 2003/0191425 A1 | 10/2003 | Rosenblatt |
| 2004/0176743 A1 | 9/2004 | Morris et al. |
| 2004/0249337 A1 | 12/2004 | DiFiore |
| 2005/0027261 A1 | 2/2005 | Weaver et al. |
| 2005/0033222 A1 | 2/2005 | Haggstrom et al. |
| 2005/0085765 A1 | 4/2005 | Voorhees |
| 2005/0090776 A1 | 4/2005 | McGuckin, Jr. et al. |
| 2005/0215978 A1 | 9/2005 | Ash |
| 2005/0228339 A1 | 10/2005 | Clark |
| 2005/0256509 A1 | 11/2005 | Sakai |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2006/0149191 A1 | 7/2006 | DiFiore |
| 2006/0253063 A1 | 11/2006 | Schweikert |
| 2007/0100298 A1 | 5/2007 | Appling |
| 2007/0219527 A1 | 9/2007 | Barron |
| 2007/0225678 A1 * | 9/2007 | Lui .............................. 604/523 |
| 2009/0312718 A1 | 12/2009 | Onuma |
| 2010/0081986 A1 | 4/2010 | Matson |

FOREIGN PATENT DOCUMENTS

| | | | |
|---|---|---|---|
| EP | 0 554 722 A1 | | 8/1993 |
| EP | 0 583 070 | | 2/1994 |
| EP | 0 322 225 B1 | | 2/1995 |
| EP | 0 713 406 B1 | | 3/1998 |
| EP | 0 864 336 A3 | | 3/1999 |
| EP | 0 570 530 B1 | | 8/1999 |
| EP | 0 555 780 B1 | | 9/1999 |
| EP | 1 595 565 A | | 11/2005 |
| EP | 1 144 039 B1 | | 12/2005 |
| EP | 1955728 A1 | | 8/2008 |
| EP | 2 119 468 A1 | | 11/2009 |
| JP | 6324958 A | | 2/1988 |
| JP | 02005975 A | | 1/1990 |
| JP | 2001321447 A | * | 11/2001 |
| JP | 2007-175297 | | 7/2007 |
| JP | 2008-126661 | | 6/2008 |
| WO | WO 95/04567 A1 | | 2/1995 |
| WO | WO 97/37699 A1 | | 10/1997 |
| WO | WO 98/41277 | | 9/1998 |
| WO | WO 99/16493 | | 4/1999 |
| WO | WO 99/38550 | | 8/1999 |
| WO | WO 99/65557 | | 12/1999 |
| WO | WO 00/06239 A2 | | 2/2000 |
| WO | WO 01/91845 A1 | | 12/2001 |
| WO | WO 02/13899 A1 | | 2/2002 |
| WO | WO 02/18004 A3 | | 3/2002 |
| WO | WO 03/033049 A3 | | 4/2003 |
| WO | WO 03/066148 A1 | | 8/2003 |
| WO | WO 2004/093956 A1 | | 11/2004 |
| WO | WO 2005/023336 A2 | | 3/2005 |
| WO | WO 2005/077449 A1 | | 8/2005 |
| WO | WO 2005/084741 A1 | | 9/2005 |
| WO | WO 2006/014339 A2 | | 2/2006 |
| WO | WO 2007/111874 A2 | | 10/2007 |

OTHER PUBLICATIONS

Office Action from Chinese Appl. No. 200910204452.0 dated Sep. 27, 2013.

Extended European Search Report corresponding to EP Application No. 09 17 0662, completed Jan. 11, 2010; completed on Jan. 11, 2010 (3 pages).

Extended European Search Report issued by the European Patent Office and completed on Sep. 22, 2009 in co-pending European Patent Application No. EP 09251289.6.

Extended European Search Report issued by the European Patent Office dated May 21, 2012 in EP Application No. 12158534.

Australian Office Action dated Sep. 14, 2012 issued in copending Australian Application No. 2012201416.

European Search Report from EP Application No. EP 13181185 mailed Sep. 26, 2013.

* cited by examiner (a)   (b)

CATHETER WITH VALVE

This application claims the benefit of and priority to Japanese Patent Application Serial No. 2011-050890 which was filed on Mar. 8, 2011, the entirety of which is incorporated herein by reference.

FIELD OF THE INVENTION

The present invention relates to a catheter with a valve comprising a tubular body made of a synthetic resin material having a valve with a slit.

BACKGROUND OF THE PRESENT INVENTION

Conventionally, a catheter is retained in a patient's body supplying drug solutions such as carcinostatic drugs and nutrients to a patient's vein temporarily or over a long period of time. In order to use this type of catheter to stably inject drug solutions, it is important that the catheter does not cause infectious diseases or complications as well as does not move and become detached. In addition to that, it is also important that the catheter does not become blocked. However, when using a catheter with an open tip, blood will permeate into the catheter and coagulate resulting in the catheter becoming blocked. In order to prevent the blockage of the catheter due to this blood coagulation, countermeasures have commonly been implemented which fill the inner cavity of the catheter with a Heparinized saline solution. Although this is the case, when implementing this type of countermeasure, there are problems of the actions to retain the catheter in a patient's body becoming cumbersome and complicated causing a burden for the health care professionals and a patient.

Thereupon, conventional catheters with a valve have been provided which are provided with a valve that does not have an open tip and is normally closed only opening when injecting a drug solution between the inside and outside of the catheter and when extracting blood. See, for example, Japanese published unexamined application S60-58167 (patent document 1) and Japanese published unexamined application 2009-273609 (patent document 2). This catheter with a valve (catheter with a bidirectional valve) is made from a flexible elastic material and in addition to the tip being closed, a linear-shaped slit is formed on the tip side. For this reason, when a predetermined differential pressure occurs between the inside and outside of this catheter with a valve, the slit will open allowing the drug solution to be injected into a vein, or the blood within a vein to be flow out into the catheter and extracted. Moreover, when a predetermined differential pressure does not occur between the inside and outside of this catheter with a valve, the slit will maintain the closed state. As a result, coagulation of blood inside the catheter is prevented.

In the conventional catheter with a valve of patent document 1, when a drug solution flows from the outside of the catheter to the inside of the catheter, the slit will open comparatively easy. Although this is the case, when blood flows from the outside of the catheter towards the inside of the catheter, there is a problem of the opposing surfaces forming the slit pressing against each other thereby making it difficult to open the slit.

In the conventional catheter with a valve of patent document 2, a predetermined portion of the tubular body is projected inward and a slit provided there. According to this configuration, the slit becomes comparatively easier to open when blood flows from the outside of the catheter to the inside of the catheter. However, while the release pressure when the valve is opened towards the inside of the catheter becomes lower, the release pressure when the valve is opened towards the outside of the catheter does not become low enough. Because of this, there is still room for improvement as far as the ease of opening is concerned.

The present invention takes the problems mentioned above into consideration and has an objective of providing a catheter with a valve that allows a solution to smoothly flow bi-directionally when a solution flows from the inside of the catheter towards the outside of the catheter and when a solution flows from the outside of the catheter towards the inside of the catheter.

SUMMARY

Means 1 to 4 for solving the above-mentioned problems are shown below.

[1] A catheter having a tubular body with a valve formed from an elastic and flexible synthetic resin material is provided and is equipped with a valve having a slit that can be opened and closed passing through the outer surface of the catheter from the inner surface of the tubular body. This catheter with a valve allows the passage of a solution from the inside of the tubular body towards the outside of the tubular body through the slit and the passage of a solution from the outside of the tubular body towards the inside of the tubular body through the slit. This catheter with a valve is also characterized by being provided with a movable wall sunken towards the inside direction of the tubular body at the tip of the tubular body and having a structure with differences in hardness in the thickness direction of the tubular body at the location of at least the movable wall. In the cross-sectional surface perpendicular to the center axis of the tubular body, the movable wall has a wall central portion located at a position close to the center axis and a wall tip member located at a position far from the center axis along with the slit that comprises the valve being formed on the wall tip member.

Therefore, the following functions and effects are obtained by the present invention of means 1. For example, if the difference between the inside and the outside of the catheter is small, the slit will not open and be maintained in a closed state. Therefore, for this case, the passage of solution through the slit will not occur in either direction. Hereupon, since the present invention provides a movable wall sunken towards the inside direction of the tubular body at the tip of the tubular body, when the external pressure of the catheter is greater than the internal pressure, it will become comparatively easy for deformations to occur in the movable wall and the slit will become easier to open on the inside of the tubular body. In other words, even at a low release pressure, the slit will become easier to open on the inside allowing the solution to smoothly pass from the outside of the tubular body to the inside of the tubular body. In addition, since the slit is formed on the movable wall tip and not at the movable wall central portion in the present invention, when the internal pressure of the catheter is greater than the external pressure, it will become comparatively easy for deformations to occur in the movable wall and the slit will become easier to open on the outside of the tubular body. In other words, even if the release pressure is low, the slit will become easier to open on the outside allowing the solution to smoothly pass from the inside of the tubular body to the outside of the tubular body through the slit. And even further, since the present invention has a structure with differences in hardness in the thickness direction at locations of the movable wall, the release pressure of the slit while releasing on the outside can be reduced by maintaining the hardness of the outside of the tubular body more than the inside. Conversely, the release pressure of the slit while releasing on the inside can be reduced by maintaining the hardness of the inside of the tubular body more than the outside.

The slit in the present invention is preferably formed so as to be extending along the center axis of the catheter with a valve when seen in a planar view although it can also be formed along an direction oblique with respect to the direction of the center axis or perpendicular to direction of the center axis. The slit can also be linear or curved when seen in a planar view. Furthermore, the cross-sectional shape (more precisely, cross-sectional shape of the locations where there is no movable wall) of the tubular body comprising the catheter with a valve in the present invention is not particularly limited and can also be round or oval for example. The cross-sectional shape of the tubular body can also have various shapes close to round or oval.

The solution in the present invention, is for example, a drug solution such as a carcinostatic drug or nutrients, or bodily fluids such as lymphatic fluid, gastric fluids, or urine, and solutions injected into a patient's vein or blood collected from a vein. The tube (body cavity) into which the catheter with a valve of the present invention includes blood vessels as well as the gastrointestinal tract such as the stomach, esophagus, small intestine, or large intestine, the urinary tract, or the trachea.

Hereupon, in the present invention the locations on the tubular body where there is at least the movable wall require a structure be provided with differences in hardness in the thickness direction of the tubular body. As a specific example and example can be illustrated of a multilayer structure formed from a plurality of layers of a synthetic resin material with differences in hardness.

[2] A catheter with a valve as set forth in means 1 wherein the tubular body is a two-layer structure comprising an outer layer of a relatively hard synthetic resin material and an inner layer of a relatively soft synthetic resin material.

Therefore, according to the present invention set forth in means 2, since the locations where there is a movable wall have a structure whose outside is hard and whose inside is soft, the release pressure of the slit while releasing on the inside can be reduced even more. For this reason, when the catheter external pressure is greater than the internal pressure, the solution will smoothly pass from the outside of the tubular body to the inside of the tubular body.

[3] A catheter with a valve as set forth in means 1 wherein the tubular body is a two-layer structure comprising an outer layer of a relatively soft synthetic resin material and an inner layer of a relatively hard synthetic resin material.

Therefore, according to the present invention set forth in means 3, since the locations where there is a movable wall have a structure whose inside is hard and whose outside is soft, the release pressure of the slit while releasing on the outside can be reduced. For this reason, when the catheter internal pressure is greater than the external pressure, the solution will smoothly pass from the inside of the tubular body to the outside of the tubular body.

Hereupon, preferred examples of the synthetic resin material comprising the outer layer and the inner layer resins having flexibility and elasticity include polyethylene, polypropylene, polyamide, polyvinyl chloride, polyurethane, silicone, and polyether block amide resin.

A method to allow differences in hardness between the outer layer and the inner layer is, for example, a method that forms both the outer layer and the inner layer using two different types of synthetic resin material with a different hardness. Another method in addition to this forms both the outer layer and the inner layer using the same type of synthetic resin material but with a different hardness. More specifically, a method can be pointed out that uses from among specific synthetic resin material a combination of a material that contains a large amount of plasticizer and a material that contains a small amount of plasticizer. Here, the hardness of the synthetic resin material is a hardness obtained when measured by a Durometer (namely, Shore hardness). For example, a relatively hard synthetic resin material can have a Shore hardness of D50 or more and D85 or less. A relatively soft synthetic resin material can have a Shore hardness of A70 or more and A100 or less. By comparison, a Shore hardness of A90 is roughly equivalent to a Shore hardness of D40.

[4] A catheter with a valve as set forth in means 2 or means 3 wherein the outer layer and the inner layer are formed using the same type of synthetic resin material with a different hardness.

Therefore, according to the present invention set forth in means 4, since the same type of synthetic resin material is used, it is easy for the resins to become familiar with each other and even if an adhesive layer is not interposed between them, they can be firmly adhered. For this reason, the reliability of the locations of the movable wall associated with the opening and closing of the slit can be improved.

Therefore, according to the present invention set forth in means 1 to means 4, a catheter with a valve can be provided that allows a bi-directional flow of a solution when a solution flows from the inside of the catheter towards the outside of the catheter, and when a solution flows from the outside of the catheter towards the inside of the catheter.

DETAILED DESCRIPTION OF EMBODIMENTS

First Embodiment

In the following, a catheter with a valve 11 of the first embodiment that embodies the present invention will be described in detail based on FIG. 1 to FIG. 3.

Figure 1:
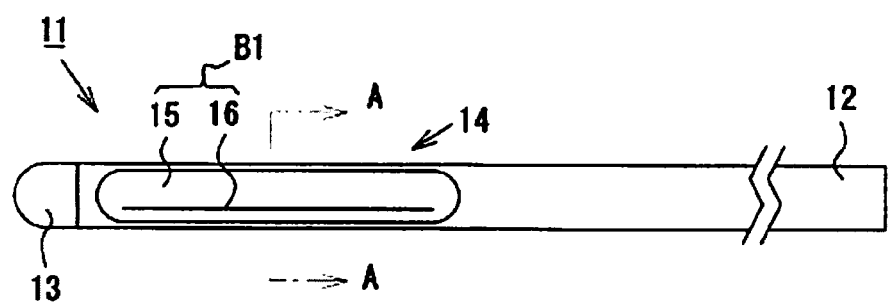
FIG. 1 a shows a partial cutaway plan view of the catheter with a valve of the first embodiment that embodies the present invention.
Figure 2:
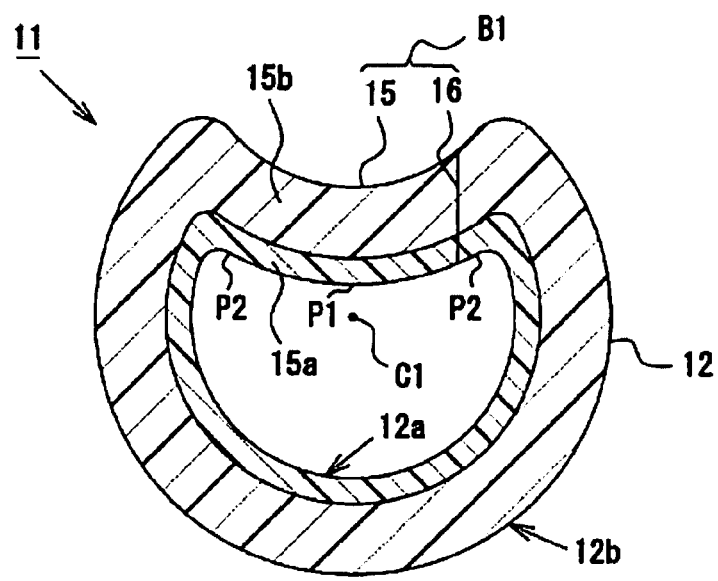
FIG. 2 a schematic cross-sectional view of line A-A of FIG. 1.
Figure 3:
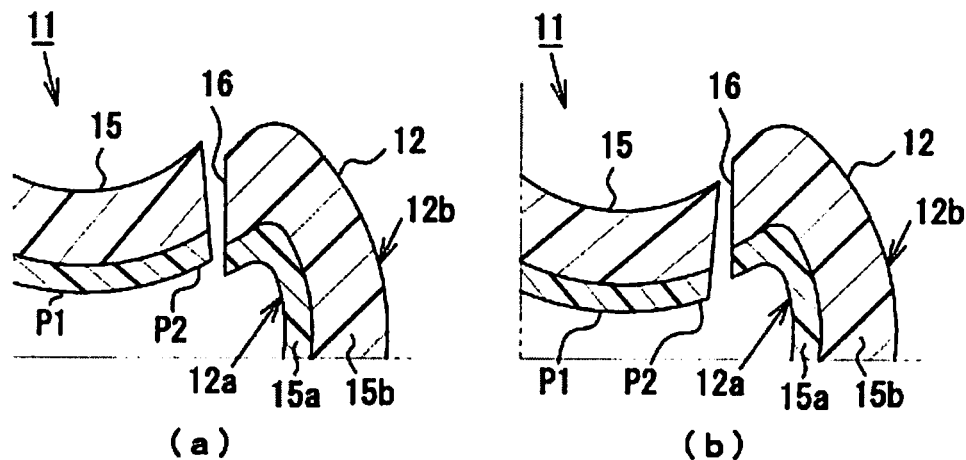
FIG. 3 is (a) is an expanded cross-sectional view of the principal parts in the catheter with a valve of the first embodiment showing a state of the slit when a solution is passing from the inside of the tubular body to the outside of the tubular body and (b) is an expanded cross-sectional view of the principal parts in the catheter with a valve of the first embodiment showing a state of the slit when a solution is passing from the outside of the tubular body to the inside of the tubular body.

As shown in FIG. 1 and FIG. 2, the catheter with a valve 11 of this embodiment is a catheter used for central veins that is retained in the vein of a patient in order to supply drug solutions such as carcinostatic drugs and nutrients. This catheter with a valve 11 is comprised by a long and thin tubular body 12 made of an elastic and flexible synthetic resin material. The base end member of the tubular body 12 is opened due to the need to connect the solution transport line. In contrast, the end tip member of the tubular body 12 is completely closed by forming a dome-shaped wall member 13 in this embodiment. This wall member 13 is formed from a soft polyurethane resin or silicone resin and is attached to the tubular body 12 comprising the catheter with a valve 11 by adhesion or weld. The base end member of the tubular body 12 can also be equipped with an adapter.

A movable wall 15 with a shape sunken towards the inside direction of the tubular body 12 is provided on the circumferential surface of the end tip member region 14 of the tubular body 12. The movable wall 15 in this embodiment has an elliptical shape extending along the longitudinal direction (direction of center axis C1) of the catheter when seen in a planar view. The movable wall 15 also has a shape curving in an arc shape evenly thick in a cross section perpendicular to the center axis C1 of the tubular body 12. This movable wall 15 has a movable wall center member P1 and a movable wall end member P2. The movable wall center member P1 is positioned relatively close to the center axis C1 and the movable wall end member P2 is positioned relatively far from the center axis C1.

As shown in FIG. 1 and FIG. 2, a linear-shaped slit 16 is formed extending along the longitudinal direction of the catheter on the movable wall 15 when seen in a planar view. In more detail, this slit 16 is formed so as to pass through from an inner surface 12a of one wall member P2 to an outer surface 12b on the movable wall 15. Moreover, this slit 16 is normally closed when there is no difference between the internal and the external pressure of the tubular body 12 or the difference is small. When the difference between the internal and the external pressure exceeds a predetermined value, the slit 16 changes and is opened. Then, a valve B1 is comprised by the movable wall 15 and the slit 16 formed on the movable wall. This valve B1 allows the passage of solution through the slit 16 from the inside of the tubular body 12 towards the outside of the tubular body 12 and the passage of solution from the outside of the tubular body 12 towards the inside of the tubular body 12 functioning as a so-called two-way valve.

As shown in FIG. 2, the tubular body 12 of this embodiment has a two-layer structure formed from an outer layer 15b and an inner layer 15a across the entire structure (namely, across the entire length and the entire circumference). In other words, the inner layer 15a is formed so as to cover the entire inside surface of the outer layer 15b. This tubular body 12 comprising a two-layer structure is manufactured by extruding the outer layer 15b and the inner layer 15a at the same time using an extrusion molding method and then integrally forming them into one member. Therefore, the outer layer 15b and the inner layer 15a are in close contact with each other regardless of whether or not an adhesive layer is interposed between them. Consequently, the locations where at least there is the movable wall 15 in the tubular body 12 in this embodiment have structure with differences in hardness in the thickness direction of the tubular body 12. Further, the slit 16 is formed passing through this type of structure difference in hardness in the thickness direction. The outer layer 15b and the inner layer 15a comprising this tubular body 12 are both formed using the same type of polyurethane resin but with a different hardness. More specifically, the material of the outer layer 15b has a Shore hardness of approximately A85 and uses a polyurethane resin that has relatively high body temperature softening properties. The material of the inner layer 15a has a Shore hardness of approximately D65 and uses a polyurethane resin that has relatively high alcohol resistance. In other words, this tubular body 12 comprises the outer layer 15b formed from a relatively soft synthetic resin material and the inner layer 15a formed from a relatively hard synthetic resin material. The thickness of the inner layer 15a in this tubular body 12 is somewhat thinner than the thickness of the outer layer 15b. It is approximately 20% to 40% the thickness of the outer layer 15b.

A method of manufacturing the catheter with a valve 11 of this embodiment will be described. The formation of the movable wall 15 can be implemented by various different methods. For example, after forming the tubular body 12 with the end tip member closed, the end tip member region 14 can also be formed into a concave shape by applying a moderately heated gas to the end tip member region 14 using a heat gun. In addition, another method is in which a moderately heated metal rod is pressed onto the end tip member region 14 of the tubular body 12 with the end tip member closed. Even further, another method is in which the tubular body 12 with the end tip member closed is covered by a heat shrink tubing and a portion of the tubing is shrunk. Then, the slit 16 can be formed by cutting the location deviated from the center point of the movable wall 15 that was formed along the longitudinal direction.

In the following, a usage method of the catheter with a valve 11 of this embodiment will be described. At first, disinfect the area around the puncture and then use a drape to provide a sterile surgical area. Next, tap into a blood vessel using an intravascular retention cannula (hereinafter, cannula) that can be divided in the longitudinal direction. Confirm the backflow of blood and then proceed with retaining only the cannula inside the blood vessel and remove the needle. Thereafter, pass the catheter with a valve 11 of this embodiment through the retained cannula and insert it into the blood vessel. Next, confirm that catheter with a valve 11 is retained at the desired position and then pull the cannula out from the blood vessel. Next, while being careful not to allow the catheter with a valve 11 to slip pull the cannula out from the puncture site. Then, divide the cannula such that the handle of the hub widens from side to side and remove the catheter with a valve 11. For this case, confirm that the catheter with a valve 11 is not drawing a loop inside the body or that the catheter tip is at the desired position using X-rays. Next, rotate the straight adapter and slowly remove the stylet from the catheter with a valve 11. Then, the catheter with a valve 11 is retained, remove the air from the inner cavity of the catheter using a saline solution or a Heparinized saline solution. Next, secure the skin using suture thread or tape and properly protect the catheter with a valve 11 over the entire length of the catheter using a dressing such that an external pressure is not applied. Lastly, connect the base tip of the catheter with a valve 11 to the solution transport line and start the injection of the drug solution. At this time, be careful not to allow any of the drug solution to adhere to the tapered portion of the adapter in order to prevent a loose connection. Furthermore, the catheter should be used after confirming in advance that there is no looseness in the connection and it is also necessary to confirm that the catheter is not loose or became disconnected during use.

When intravenously supplying a drug solution to a patient through the catheter with a valve 11 retained in a blood vessel, initially, connect the solution transport line, filled with the drug solution, to the catheter base end member. Next, inject the drug solution. At this time, the pressure applied to the drug solution from a syringe (namely, a internal pressure of the catheter) will become greater than the blood pressure inside the superior vena cava (namely, the external pressure of the catheter). Because of this, the movable wall 15 deforms comparatively easy on the outside of the catheter with a valve 11 as shown in FIG. 3(*a*) thereby causing the slit 16 to open. As a result, the drug solution smoothly passes from the inside of the tubular body 12 to the outside of the tubular body 12 through the open slit 16 moving into the superior vena cava.

Moreover, while collecting blood and confirming the back-flow of blood, connect a syringe, that is in a state evacuating internally, to the base end member of the catheter. Thereafter, pull the plunger of the syringe. At this time, the pressure (namely, internal pressure of catheter) applied to the drug solution from a syringe by the suction force of the syringe becomes smaller than the blood pressure (namely, external pressure of catheter) in the superior vena cava. For this reason, the movable wall 15 deforms comparatively easy as shown in FIG. 3(*b*) thereby causing the slit 16 to open. As a result, the blood in the vein smoothly passes from the outside of the tubular body 12 to the inside of the tubular body 12, through the open slit 16, through the tubular body 12 and into the syringe.

However, when a syringe is not injecting any drug solution nor drawing out any blood, slit 16 will be maintained in a closed state by the restorative force produced by the elasticity of the movable wall 15. Therefore, for this case, the passage of blood and solution through the slit 16 will not occur in either direction.

The following functions and effects are obtained according to this embodiment as described above.

(1) The catheter with a valve 11 of this embodiment is provided with the movable wall 15 sunken towards the inside direction of the tubular body 12 and the slit 16 is provided there. Because of this, when the external pressure of the catheter is greater than the internal pressure, it will become comparatively easy for deformations to occur in the movable wall 15 and the slit 16 will become easier to open on the inside of the tubular body 12. In other words, even at a low release pressure, the slit 16 will become easier to open on the inside allowing the blood to smoothly pass from the outside of the tubular body 12 to the inside of the tubular body 12. Furthermore, the slit 16 is formed on the movable wall end member P2 and not on the movable wall center member P1 in this catheter with a valve 11. Therefore, when the internal pressure of the catheter is greater than the external pressure, it will become comparatively easy for deformations to occur in the movable wall 15 and the slit 16 will become easier to open on the outside of the tubular body 12. In other words, even if the release pressure is low, the slit 16 will become easier to open on the outside allowing the drug solution to smoothly pass from the inside of the tubular body 12 to the outside of the tubular body 12 through the slit 16.

(2) For example, when the outer layer 15*a* and the inner layer 15*b* are different types of synthetic resin materials, they must be adhered to each other through an adhesive layer thereby increasing the complexity of the structure and making it difficult to obtain a strong adhesion state. In addition, since especially the locations of the movable wall 15 associated with the opening and closing of the slit 16 frequently deform, there is a possibility that peeling will occur at the interface between the inner layer 15*b* and the outer layer 15*a*. In that respect, in the catheter with a valve 11 of this embodiment, the tubular body 12 is a two-layer structure comprising the outer layer 15*b* of a relatively soft polyurethane resin and the inner layer 15*a* of a relatively hard polyurethane resin. Therefore, since the outer layer 15*b* and the inner layer 15*a* are the same type of synthetic resin material, they are compatible and it is easy for the resins to become familiar with each other. For this reason, even if a specific adhesive layer is not interposed between them, they can be firmly adhered to each other during the extrusion molding. And because of this, peeling of the locations of the movable wall 16 associated with the opening and closing of the slit 16 becomes difficult to occur and the reliability can be improved.

Second Embodiment

Figure 4:
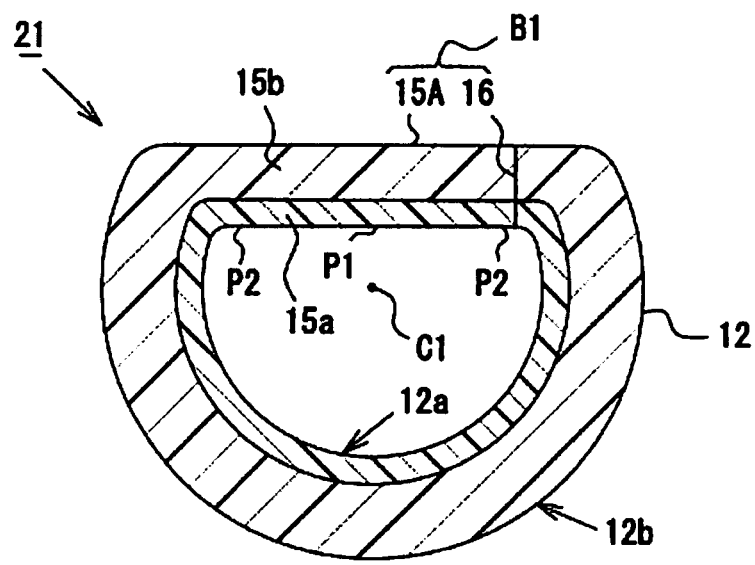
FIG. 4 is a schematic cross-sectional view showing the tip member region of the second embodiment of the catheter that embodies the present invention.

In the first embodiment, although the movable wall 15 had a shape curving in an arc shape in a cross section perpendicular to the center axis C1 of the tubular body 12, there is no limitation to this. For example, the movable wall 15A can also be linear in like manner to the catheter with a valve 21 in the second embodiment shown in FIG. 4. Even if this type of structure is used functions and effects similar to the first embodiment can be obtained. Moreover, the movable wall can have a cross-sectional shape other than an arc shape or a linear shape such as a cross-sectional shape bent into a V-shape.

Third Embodiment

Figure 5:
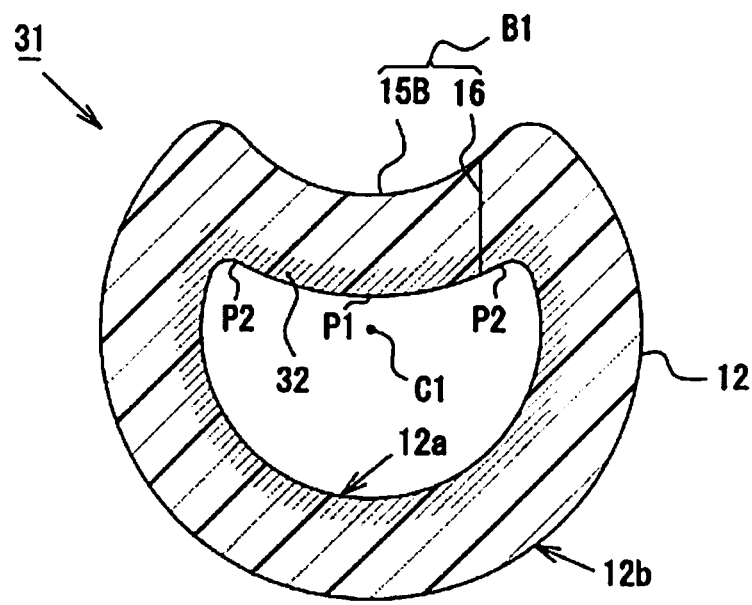
FIG. 5 is a schematic cross-sectional view showing the tip member region of the third embodiment of the catheter that embodies the present invention.

Although the tubular body 12 of the catheter with a valve 11 of the first embodiment had a two-layer structure comprising the outer layer 15*b* of a relatively hard synthetic resin material and the inner layer 15*a* of a relatively soft synthetic resin material, there is no limitation to this. For example, the tubular body 12 of the catheter with a valve 31 of the third embodiment shown in FIG. 5 does not need to have a specific layered structure but can be formed from one type of synthetic resin material (polyurethane resin here). And instead of this, the side of the inner surface 12*a* is hardened by a method such as a chemical treatment. By comparison, FIG. 5 shows a rough hatching of a portion of the original resin as well as shows dense hatching of a hardened portion of resin (curing process member 32). Therefore, the movable wall 15B of the catheter with a valve 31 of the third embodiment also has a structure with a difference in hardness in the thickness direction of the tubular body 12. Even if this type of structure is used, functions and effects similar to the first embodiment can be obtained. Moreover, contrary to this embodiment, the side of the outer surface 12*b* can also be hardened by a method such as chemical treatment. Even further, the side of the outer surface 12*b* or the side of the inner surface 12*a* can also be softened by a method such as chemical treatment.

Fourth Embodiment

Figure 6:
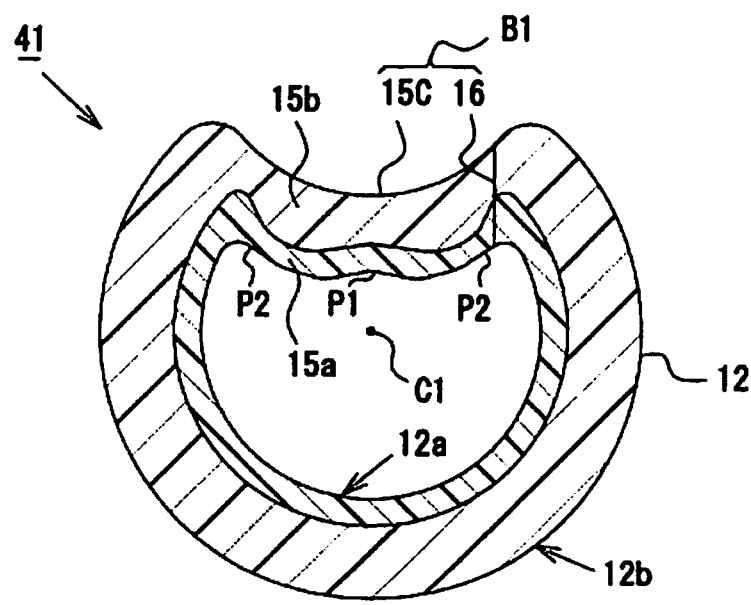
FIG. 6 is a schematic cross-sectional view showing the tip member region of the fourth embodiment of the catheter that embodies the present invention.

Although the thickness of the outer layer 15*b* and the inner layer 15*a* of the movable wall 15 of the catheter with a valve 11 of the first embodiment was almost a constant thickness and the ratio of the thickness of the two layers was almost a constant, it does not always have to be that way. For example, the thickness of the outer layer 15*b* and the inner layer 15*a* of the movable wall 15C of the catheter with a valve 41 of the fourth embodiment shown in FIG. 6 can be different depending on the location. More specifically, while the thickness of the movable wall end member P2 is the most thin at the outer layer 15*b*, the thickness of the movable wall end member P2 is the most thick at the inner layer 15*a*. Therefore, the thickness of the outer layer 15*b* at the movable wall center member P1 is somewhat thicker than the thickness of the inner layer 15*a* while the thickness of the outer layer 15*b* at the movable wall end member P2 is equal to the thickness of the inner layer 15a. Even if this type of structure is used, functions and effects similar to the first embodiment can be obtained.

Fifth Embodiment

Figure 7:
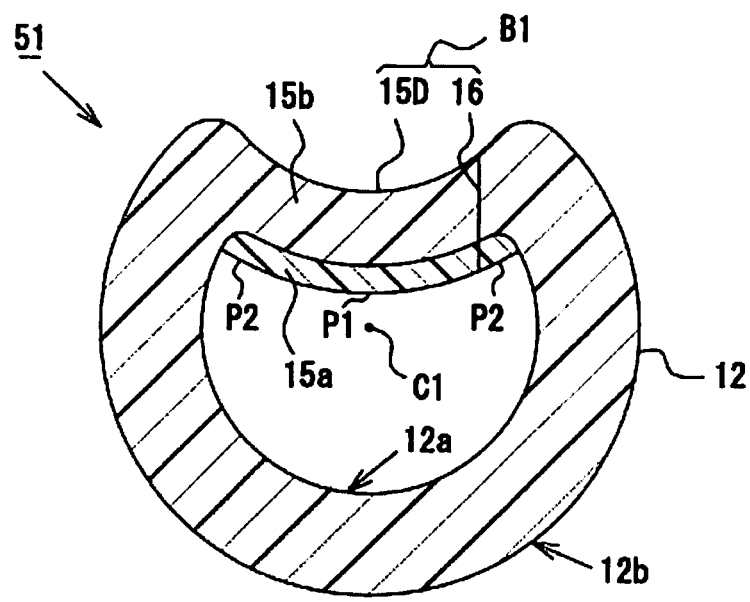
FIG. 7 is a schematic cross-sectional view showing the tip member region of the fifth embodiment of the catheter that embodies the present invention.

Although the tubular body 12 of the catheter with a valve 11 of the first embodiment had a two-layer structure across the entire structure comprising the outer layer 15b and the inner layer 15a, it does not always have to be that way. For example, in the catheter with a valve 51 of the fifth embodiment shown in FIG. 7, instead of the inner layer 15a being formed so as to cover the entire inner surface of the outer layer 15b, the inner layer 15a is formed so as to only cover the inner surface of the side where the movable wall 15D exists. Moreover, as shown in FIG. 7, the thickness of the tubular body 12 is almost constant regardless of the portion of the two-layer structure and the portion of the one-layer structure. Even if this type of structure is used, functions and effects similar to the first embodiment can be obtained.

Sixth Embodiment

Figure 8:
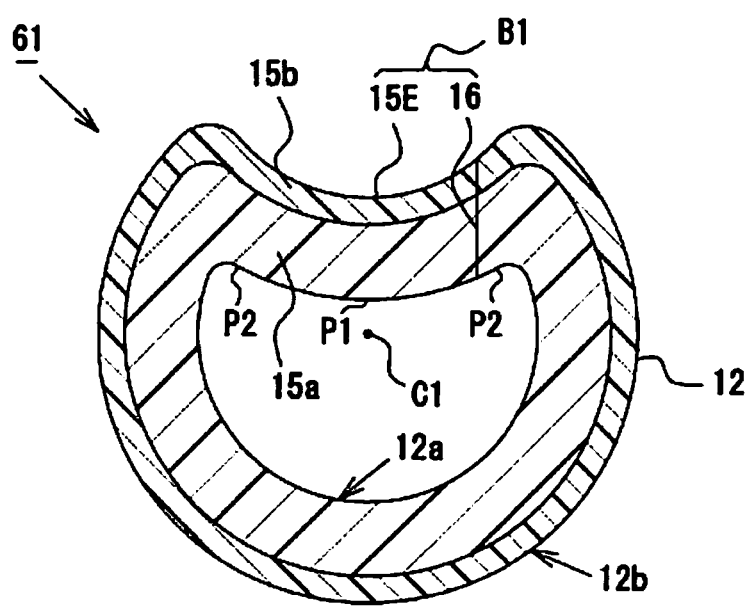
FIG. 8 is a schematic cross-sectional view showing the tip member region of the sixth embodiment of the catheter that embodies the present invention.

The tubular body 12 of the catheter with a valve 11 of the first embodiment had a two-layer structure comprising the outer layer 15b of a relatively soft synthetic resin material and the inner layer 15a of a relatively hard synthetic resin material. In contrast to this, the tubular body 12 of the catheter with a valve 61 of the sixth embodiment shown in FIG. 8 has a two-layer structure comprising the outer layer 15b of a relatively hard resin material and the inner layer 15a of a relatively soft resin material. Therefore, according to this composition, since the structure has a hard outside and a soft inside at locations where the movable wall 15E exists, the release pressure of the slit 16 while releasing on the outside can be reduced even more. For this reason, when the catheter external pressure is greater than the internal pressure, blood can smoothly pass from the outside of the tubular body 12 to the inside of the tubular body 12 through the slit 16.

The embodiment of the present invention may be modified as follows.

Although each of the above-mentioned catheters with a valve 11 to 61 are provided with one movable wall 15 to 15E in the tubular body 12 along with the slit 16 being formed at one location on the movable wall 15 to 15E, the slit 16 can also be formed at multiple locations. In addition, the movable wall 15 to 15E can be provided at multiple locations of the tubular body 12.

In each of the above-mentioned embodiments, although the base end member of the catheter with a valve 11 to 61 was drawn outside the body along with a solution transport line connected to the base end member and used, instead of this, a syringe can also be connected and used. Furthermore, the base end member can be connected to an implant port inside the body and this implant port inside the body embedded under the skin and used. Even further, in each of the above-mentioned embodiments, although the catheter with a valve 11 to 61 is retained in a vein, it is also possible to use a certain means to retain the catheter in an artery.

Although no special material was contained in the inner cavity of the catheter with a valve 11 to 61 of each of the above-mentioned embodiments, the structure can be such that a linear member, such as a guide wire, is inserted. For this case, a normally closed slit can be provided on the end tip member of the tubular body 12 that comprises the catheter with a valve 11 to 61 and the slit pressed and opened as necessary to allow the end tip of the guide wire to protrude from the catheter with a value 11.

In the catheter with a valve 11 of the above-mentioned first embodiment, although the outer layer 15b and the inner layer 15a were basically comprised by only a synthetic resin material, a material other than a synthetic resin material can also be added. For example, a material impermeable to X-rays such as gold, silver, platinum, tungsten, a metal powder formed from an alloy of these, barium sulfate, or bismuth oxide can be mixed into this synthetic resin material so as to allow the position and condition of the catheter with a valve 11 under fluoroscopic control during use. For this as well, adjustments can be made to provide differences in hardness of both the outer layer 15b and the inner layer 15a by suitably changing the type, the quantity, and the size.

In each of the above-mentioned embodiments, although the structure was such that there were differences in hardness in the thickness direction of the tubular body 12 at the location of the movable wall 15 to 15E on the tubular body 12, in place of this, a structure can also be provided that has a difference in elasticity in the thickness direction of the tubular body 12. For example, the outer layer 15b on the tubular body 12 can be formed from a synthetic resin material with a relatively high coefficient of elasticity and the inner layer 15a can be formed from a synthetic resin material with a relatively low coefficient of elasticity. Conversely, the outer layer 15b on the tubular body 12 can be formed from a synthetic resin material with a relatively low coefficient of elasticity and the inner layer 15a can be formed from a synthetic resin material with a relatively high coefficient of elasticity. Even if this type of structure is provided, functions and effects similar to a structure with differences in hardness can be expected. As an example for this case, the outer layer 15b and the inner layer 15a can be formed using the same type of synthetic resin material with different coefficients of elasticity.

Although the catheter with a valve 11 to 61 of each of the above-mentioned embodiments was a single-lumen type having only one inner cavity, it can be a double-lumen type having two inner cavities or a triple-lumen type having three inner cavities.

The technical concepts understood from the embodiments of the present invention are presented below.

(1) A catheter with a valve is formed from an elastic and flexible synthetic resin material and is equipped with a valve having a slit that can be opened and closed passing through the outer surface from the inner surface of the tubular body. This catheter with a valve is characterized by allowing the passage of a solution from the inside of the tubular body towards the outside of the tubular body through the slit and the passage of a solution from the outside of the tubular body towards the inside of the tubular body through the slit. It is also provided with a movable wall sunken towards the inside direction of the tubular body at the tip of the tubular body and has a structure with differences in hardness in the thickness direction of the tubular body at the location of at least the movable wall, and in the cross-sectional surface perpendicular to the center axis of the tubular body the movable wall has a wall central portion located at a position close to the center axis and a wall tip member located at a position far from the center axis along with the slit comprising the valve being formed on the wall tip member.

(2) The catheter with a valve as set forth in concept 1 wherein the tubular body is a two-layer structure comprising an outer layer of a relatively hard synthetic resin material and an inner layer of a relatively soft synthetic resin material.

(3) The catheter with a valve as set forth in concept 1 can be formed from a tubular body which is a two-layer structure comprising an outer layer of a synthetic resin material with a relatively low coefficient of elasticity and an inner layer of a synthetic resin material with a relatively high coefficient of elasticity.

(4) In the catheter with a valve as set forth in concept 2 or concept 3, the outer layer and the inner layer can be formed using the same type of synthetic resin material with a different coefficient of elasticity.

(5) In any of the above-mentioned means 1 to means 4 or the above-mentioned concept 1 to concept 4, the tubular body should be comprised such that the tip is normally closed.

(6) In any of the above-mentioned means 1 to means 4 or the above-mentioned concept 1 to concept 4, the tubular body should have a slit that can open and close at the tip along with being comprised such that the slit is normally closed.

(7) In any of the above-mentioned means 1 to means 4 or the above-mentioned concept 1 to concept 4, the movable wall should have an arc-shaped cross section.

(8) In any of the above-mentioned means 1 to means 4 or the above-mentioned concept 1 to concept 4, the tubular body should be provided with a two-layer structure across the entire body.

(9) In any of the above-mentioned means 2 to means 4 or the above-mentioned concept 2 to concept 4, the inner layer should be thinner than the outer layer.

(10) In any of the above-mentioned means 2 to means 4 or the above-mentioned concept 2 to concept 4, the tubular body should be an extrusion molded part.

(11) In any of the above-mentioned means 2 to means 4 or the above-mentioned concept 2 to concept 4, an adhesive layer should not exist between the interface between the outer layer and the inner layer.

(12) In any of the above-mentioned means 2 to means 4 or the above-mentioned concept 2 to concept 4, the synthetic resin material forming the outer layer and the inner layer should be a polyurethane resin.

(13) In any of the above-mentioned means 2 to means 4 or the above-mentioned concept 2 to concept 4, the outer layer should have high body temperature softening properties compared to the inner layer and the inner layer should have high chemical resistance properties compared to the outer layer.

The invention claimed is:

1. A catheter having a tubular body formed from an elastic and flexible synthetic resin material and being equipped with a valve having a slit that can be opened and closed, the slit passing through an outer surface of the tubular body from an inner surface of the tubular body, the catheter being characterized by allowing passage of a solution from the inside of the tubular body towards the outside of the tubular body through the slit and passage of a solution from the outside of the tubular body towards the inside of the tubular body through the slit, the catheter being provided with a movable wall sunken towards the inside of the tubular body at a tip of the tubular body, at least the movable wall having differences in hardness in the thickness direction of the tubular body, and in the cross-sectional surface perpendicular to the center axis of the tubular body, the movable wall having a wall central portion located at a position close to the center axis and a wall tip member located at a position far from the center axis along with the slit comprising the valve being formed on the wall tip member.

2. The catheter with a valve as set forth in claim 1, wherein the tubular body is a two-layer structure comprising an outer layer of a relatively hard synthetic resin material and an inner layer of a relatively soft synthetic resin material.

3. The catheter with a valve as set forth in claim 1, wherein the tubular body is a two-layer structure comprising an outer layer of a relatively soft synthetic resin material and an inner layer of a relatively hard synthetic resin material.

4. The catheter with a valve as set forth in claim 2, wherein the outer layer and the inner layer are formed using the same type of synthetic resin material with a different hardness.

5. The catheter with a valve as set forth in claim 3, wherein the outer layer and the inner layer are formed using the same type of synthetic resin material with a different hardness.

* * * * *